(12) United States Patent
Ishihara et al.

(10) Patent No.: US 10,927,206 B2
(45) Date of Patent: Feb. 23, 2021

(54) COPOLYMER AND APPLICATION THEREFOR

(71) Applicants: NOF CORPORATION, Tokyo (JP); THE UNIVERSITY OF TOKYO, Tokyo (JP)

(72) Inventors: Kazuhiko Ishihara, Tokyo (JP); Masaru Matsuda, Kawasaki (JP); Tomozumi Noda, Kawasaki (JP); Satoshi Yamada, Kawasaki (JP); Nobuyuki Sakamoto, Kawasaki (JP)

(73) Assignees: NOF CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 116 days.

(21) Appl. No.: 16/313,292

(22) PCT Filed: Jun. 28, 2017

(86) PCT No.: PCT/JP2017/023654
§ 371 (c)(1),
(2) Date: Dec. 26, 2018

(87) PCT Pub. No.: WO2018/003821
PCT Pub. Date: Jan. 4, 2018

(65) Prior Publication Data
US 2019/0153137 A1 May 23, 2019

(30) Foreign Application Priority Data
Jun. 29, 2016 (JP) ................. 2016-129411

(51) Int. Cl.
| | | |
|---|---|---|
| *C08F 230/02* | (2006.01) | |
| *C08F 212/08* | (2006.01) | |
| *C08F 220/18* | (2006.01) | |
| *C08J 3/28* | (2006.01) | |
| *A61L 27/34* | (2006.01) | |
| *A61L 33/06* | (2006.01) | |
| *C08J 3/24* | (2006.01) | |
| *C09D 143/02* | (2006.01) | |
| *C08J 7/04* | (2020.01) | |
| *C08F 12/22* | (2006.01) | |
| *C08F 12/26* | (2006.01) | |

(52) U.S. Cl.
CPC ............ *C08F 230/02* (2013.01); *A61L 27/34* (2013.01); *A61L 33/06* (2013.01); *C08F 212/08* (2013.01); *C08F 220/18* (2013.01); *C08J 3/24* (2013.01); *C08J 3/28* (2013.01); *C08J 7/0427* (2020.01); *C09D 143/02* (2013.01); *A61L 33/064* (2013.01); *A61L 2400/18* (2013.01); *C08F 12/22* (2013.01); *C08F 12/26* (2013.01); *C08F 220/1818* (2020.02); *C08J 2325/06* (2013.01); *C08J 2453/00* (2013.01)

(58) Field of Classification Search
CPC .... C08F 230/02; C08F 212/08; C08F 220/18; C08J 3/28; A61L 33/064; A61L 27/34
See application file for complete search history.

(56) References Cited

U.S. PATENT DOCUMENTS 10,323,132 B2 * 6/2019 Ishihara ................. A61L 31/14

OTHER PUBLICATIONS

Lin et al, Photoreactive Polymers Bearing a Zwitterionic Phosphorylchloline Group for Surface Modification of Biomaterials, ACS Appl. Mater, Interfaces (2015) 7, pp. 17498-17498 (Year: 2015).*

* cited by examiner

*Primary Examiner* — Robert D Harlan
(74) *Attorney, Agent, or Firm* — Sughrue Mion, PLLC

(57) ABSTRACT

Provided are a copolymer having biocompatibility sufficient for use in medical material applications, and a method of forming a crosslinked body, the method including imparting biocompatibility to a substrate surface through the use of the copolymer. More specifically, a protein adsorption-suppressing effect and a cell adhesion-suppressing effect, which are features of a phosphorylcholine group, are imparted to the substrate surface. It has been found that a copolymer containing a phosphorylcholine constitutional unit and a photoreactive constitutional unit, or a copolymer containing a phosphorylcholine constitutional unit, a photoreactive constitutional unit, and a hydrophobic constitutional unit can impart a protein adsorption-suppressing effect and a cell adhesion-suppressing effect to a substrate surface through a simple approach called photoirradiation.

18 Claims, No Drawings

COPOLYMER AND APPLICATION THEREFOR

CROSS REFERENCE TO RELATED APPLICATIONS

This Application is a National Stage of International Application No. PCT/JP2017/023654 filed Jun. 28, 2017, claiming priority based on Japanese Patent Application No. 2016-129411 filed Jun. 29, 2016 incorporated herein by reference.

TECHNICAL FIELD

The present invention relates to a copolymer and an application therefor.

BACKGROUND ART

A phosphorylcholine group-containing copolymer has excellent biocompatibility typified by blood compatibility. Accordingly, the phosphorylcholine group-containing copolymer has been utilized in an application where a coating of the copolymer is formed on the surface of a substrate poor in biocompatibility to make the surface biocompatible. For example, the copolymer has been utilized in surface treatment agents for various medical devices, such as an artificial heart, an artificial lung, an artificial vessel, and a contact lens (Non Patent Literature 1).

In such application, the copolymer is often used as described below. The copolymer is bonded to the substrate surface to which biocompatibility is to be imparted through physical bonding or chemical bonding to form a hydrous coating gel on the substrate surface. In order to perform the physical bonding on the substrate surface, for example, a method involving introducing a monomer having a hydrophobic group into the copolymer having a phosphorylcholine group to perform the physical bonding, or a method involving introducing an ionic group into the copolymer to perform ionic bonding is used.

In each of those methods, however, part of the structure of the copolymer needs to be substituted with another functional group, and hence the function of a phosphorylcholine group cannot be sufficiently exhibited. Further, when an affinity between the copolymer and the substrate is insufficient, the durability of the coating becomes insufficient and hence the coating peels. Meanwhile, a phosphorylcholine group-containing copolymer having introduced thereinto a chemical bonding group is chemically bonded to the substrate surface. Accordingly, even when the number of functional groups to be introduced is small, the copolymer is bonded to the substrate and hence a coating having relatively high durability can be formed (Patent Literature 1). However, when the chemical bonding group is introduced, the presence of a functional group on the substrate surface is an indispensable condition. In addition, in general, bonding between molecules of the phosphorylcholine group-containing copolymer does not occur, and hence the durability has not been sufficient. Further, the step of inactivating an unreacted functional group at the time of the chemical bonding through posttreatment is also required, and hence the phosphorylcholine group-containing copolymer having introduced thereinto a chemical bonding group has involved many problems in practical use.

In view of the foregoing, a phosphorylcholine group-containing copolymer having photoreactivity has been proposed (Patent Literature 2). Even when a substrate having no chemical bonding functional group on its surface is selected, the copolymer can be bonded to the surface of the substrate. In addition, the copolymer is excellent in coating formability. However, an acid chloride and a halogen solvent are used at the time of the production of a monomer having a photoreactive azide group to be bonded to the surface of the substrate, and hence sufficient management has been needed to secure safety at the time of the production.

CITATION LIST

Patent Literature

[PTL 1] U.S. Pat. No. 6,090,901 B2
[PTL 2] JP 2010-059367 A

Non Patent Literature

[NPL 1] Kazuhiko Ishihara, MMJ the Mainichi medical journal, "Medical Forest: Prospects for the Future (2): New Material for Medical Use "MPC Copolymer"", 2010, Vol. 6, No. 2, p. 68-70

SUMMARY OF INVENTION

Technical Problem

A sufficient pursuit has not been made on a copolymer that has a photoreactive group to be bonded to a substrate surface to be made biocompatible and that is used for forming a stable crosslinked body for covering the surface.

That is, an object of the present invention is to provide a copolymer having biocompatibility sufficient for use in medical material applications, and a method of forming a crosslinked body, the method including imparting biocompatibility to a substrate surface through the use of the copolymer. More specifically, the object is to impart a protein adsorption-suppressing effect and a cell adhesion-suppressing effect, which are features of a phosphorylcholine group, to the substrate surface.

Solution to Problem

The inventors of the present invention have made extensive investigations in view of the object, and as a result, have found that a copolymer containing a phosphorylcholine constitutional unit and a photoreactive constitutional unit, or a copolymer containing a phosphorylcholine constitutional unit, a photoreactive constitutional unit, and a hydrophobic constitutional unit can impart a protein adsorption-suppressing effect and a cell adhesion-suppressing effect to a substrate surface through a simple approach called photoirradiation. Thus, the inventors have completed the present invention.

That is, the present invention is as described below.

[1] A copolymer having a weight-average molecular weight of from 10,000 to 1,000,000, the copolymer including a structure represented by the formula (1), wherein molar ratios a and b of respective constitutional units in the formula (1) satisfy the following:
a/(a+b)=0.75 to 0.99; and
b/(a+b)=0.01 to 0.25;

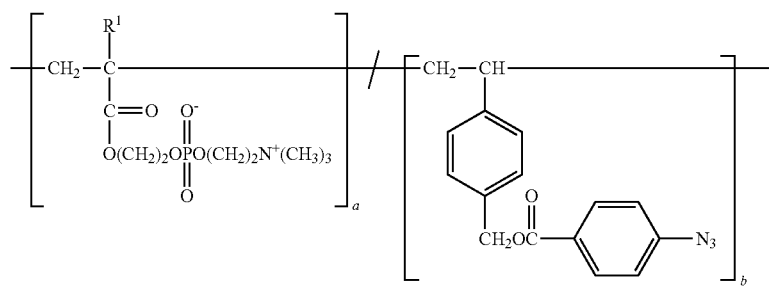 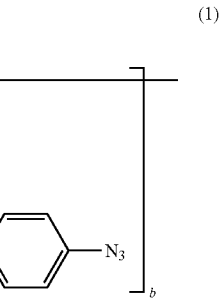

(1)

in the formula (1), $R^1$ represents a hydrogen atom or a methyl group.

[2] A copolymer having a weight-average molecular weight of from 10,000 to 1,000,000, the copolymer including a structure represented by the formula (2), wherein molar ratios a, b, and c of respective constitutional units in the formula (2) satisfy the following:
a/(a+b+c)=0.30 to 0.98;
b/(a+b+c)=0.01 to 0.25; and
c/(a+b+c)=0.01 to 0.69;

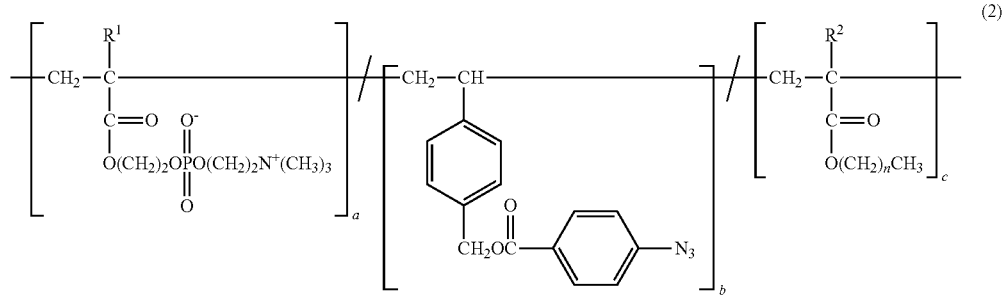 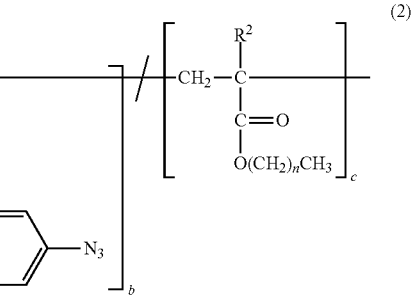

(2)

in the formula (2), $R^1$ and $R^2$ each represent a hydrogen atom or a methyl group, and n represents from 3 to 17.

[3] A copolymer according to the above-mentioned item [1], wherein the copolymer includes a constitutional unit based on 2-methacryloyloxyethyl-2-trimethylammonioethyl phosphate and a constitutional unit based on 4-(4-azidobenzoyloxymethyl)styrene.

[4] A copolymer according to the above-mentioned item [2], wherein the copolymer includes a constitutional unit based on 2-methacryloyloxyethyl-2-trimethylammonioethyl phosphate, a constitutional unit based on 4-(4-azidobenzoyloxymethyl)styrene, and a constitutional unit based on butyl methacrylate.

[5] A copolymer according to the above-mentioned item [2], wherein the copolymer includes a constitutional unit based on 2-methacryloyloxyethyl-2-trimethylammonioethyl phosphate, a constitutional unit based on 4-(4-azidobenzoyloxymethyl)styrene, and a constitutional unit based on stearyl methacrylate.

[6] A surface treatment agent, including the copolymer of any one of the above-mentioned items [1] to [5].

[7] A surface treatment agent according to the above-mentioned item [6], wherein the surface treatment agent includes a surface treatment agent for suppressing protein adsorption.

[8] A surface treatment agent according to the above-mentioned item [6], wherein the surface treatment agent includes a surface treatment agent for suppressing cell adhesion.

[9] A method of forming a crosslinked body, including: coating a substrate surface with the copolymer of any one of the above-mentioned items [1] to [5] or the surface treatment agent of any one of the above-mentioned items [6] to [8]; and then irradiating the substrate surface with light to form the crosslinked body on the substrate surface.

[10] A crosslinked body, which is obtained by the method of forming a crosslinked body of the above-mentioned item [9].

[11] A crosslinked body, which is obtained by irradiating the copolymer of any one of the above-mentioned items [1] to [5] or the surface treatment agent of any one of the above-mentioned items [6] to [8] with light.

[12] A medical device, including the crosslinked body of the above-mentioned item [10] or [11].

[13] A surface treatment agent, including a copolymer having a weight-average molecular weight of from 10,000 to 1,000,000, the copolymer including a structure represented by the formula (1), wherein molar ratios a and b of respective constitutional units in the formula (1) satisfy the following:
a/(a+b)=0.75 to 0.99; and
b/(a+b)=0.01 to 0.25;

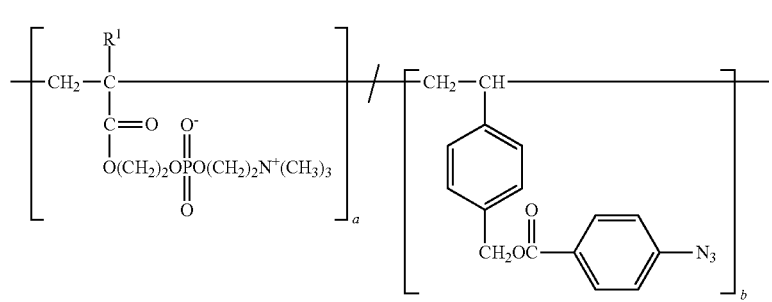

in the formula (1), $R^1$ represents a hydrogen atom or a methyl group.

[14] A surface treatment agent, including a copolymer having a weight-average molecular weight of from 10,000 to 1,000,000, the copolymer including a structure represented by the formula (2), wherein molar ratios a, b, and c of respective constitutional units in the formula (2) satisfy the following:

a/(a+b+c)=0.30 to 0.98;
b/(a+b+c)=0.01 to 0.25; and
c/(a+b+c)=0.01 to 0.69;

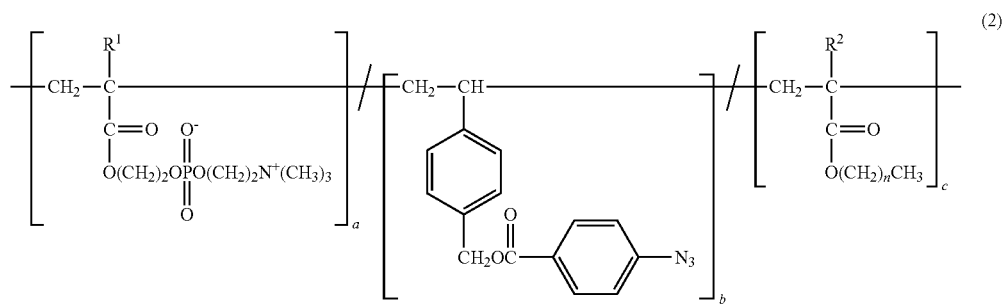

in the formula (2), $R^1$ and $R^2$ each represent a hydrogen atom or a methyl group, and n represents from 3 to 17.

[15] A surface treatment method, including using a copolymer having a weight-average molecular weight of from 10,000 to 1,000,000, the copolymer including a structure represented by the formula (1), wherein molar ratios a and b of respective constitutional units in the formula (1) satisfy the following:

a/(a+b)=0.75 to 0.99; and
b/(a+b)=0.01 to 0.25;

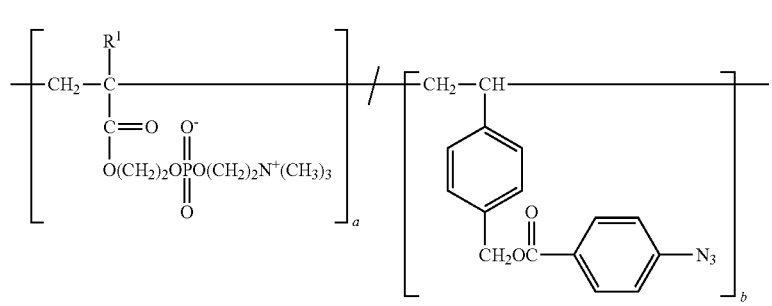

in the formula (1), $R^1$ represents a hydrogen atom or a methyl group.

[16] A surface treatment method, including using a copolymer having a weight-average molecular weight of from 10,000 to 1,000,000, the copolymer including a structure represented by the formula (2), wherein molar ratios a, b, and c of respective constitutional units in the formula (2) satisfy the following:

a/(a+b+c)=0.30 to 0.98;
b/(a+b+c)=0.01 to 0.25; and
c/(a+b+c)=0.01 to 0.69;

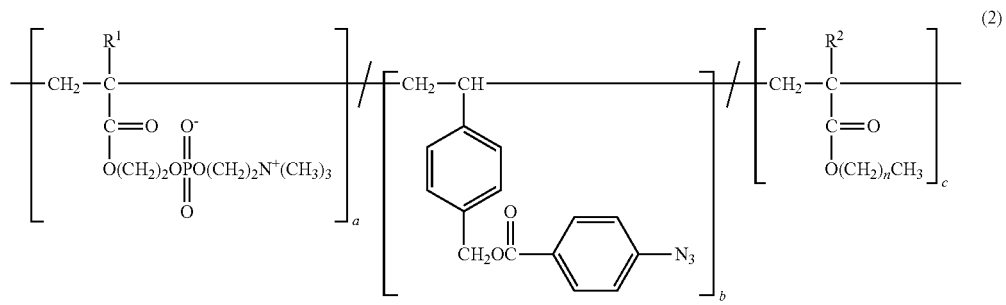

(2)

in the formula (2), $R^1$ and $R^2$ each represent a hydrogen atom or a methyl group, and n represents from 3 to 17.

[17] A copolymer for surface treatment having a weight-average molecular weight of from 10,000 to 1,000,000, the copolymer including a structure represented by the formula (1), wherein molar ratios a and b of respective constitutional units in the formula (1) satisfy the following:

a/(a+b)=0.75 to 0.99; and
b/(a+b)=0.01 to 0.25;

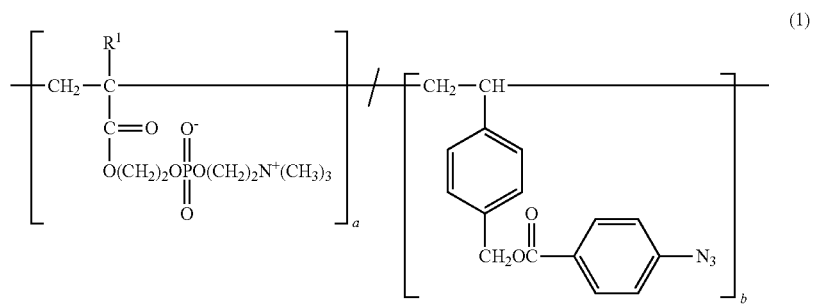

(1)

in the formula (1), $R^1$ represents a hydrogen atom or a methyl group.

[18] A copolymer for surface treatment having a weight-average molecular weight of from 10,000 to 1,000, 000, the copolymer including a structure represented by the formula (2), wherein molar ratios a, b, and c of respective constitutional units in the formula (2) satisfy the following:

a/(a+b+c)=0.30 to 0.98;
b/(a+b+c)=0.01 to 0.25; and
c/(a+b+c)=0.01 to 0.69;

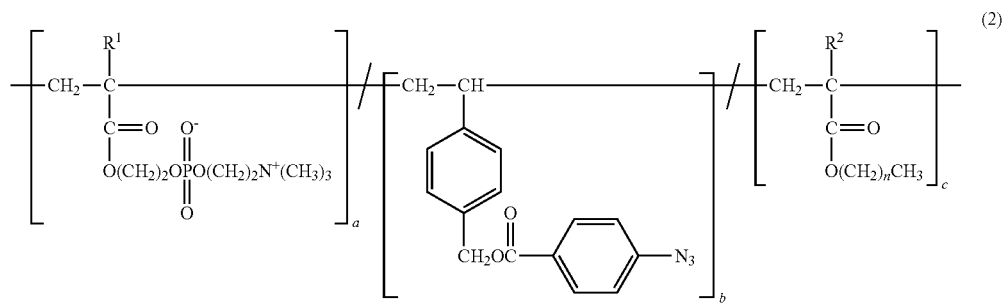

(2)

in the formula (2), $R^1$ and $R^2$ each represent a hydrogen atom or a methyl group, and n represents from 3 to 17.

[19] A use of a copolymer having a weight-average molecular weight of from 10,000 to 1,000,000, the copolymer including a structure represented by the formula (1), wherein molar ratios a and b of respective constitutional units in the formula (1) satisfy the following, in production of a surface treatment agent:

a/(a+b)=0.75 to 0.99; and
b/(a+b)=0.01 to 0.25;

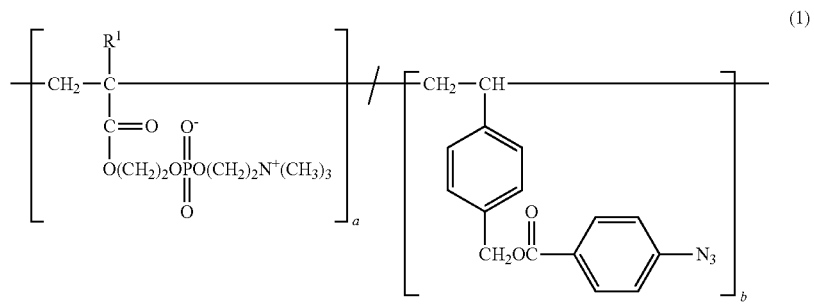

(1)

in the formula (1), $R^1$ represents a hydrogen atom or a methyl group.

[20] A use of a copolymer having a weight-average molecular weight of from 10,000 to 1,000,000, the copolymer including a structure represented by the formula (2), wherein molar ratios a, b, and c of respective constitutional units in the formula (2) satisfy the following, in production of a surface treatment agent:

a/(a+b+c)=0.30 to 0.98;
b/(a+b+c)=0.01 to 0.25; and
c/(a+b+c)=0.01 to 0.69;

in the formula (2), $R^1$ and $R^2$ each represent a hydrogen atom or a methyl group, and n represents from 3 to 17.

Advantageous Effects of Invention

According to the present invention, the copolymer having biocompatibility sufficient for use in medical material applications, and the method of forming a crosslinked body, the method including imparting biocompatibility to a substrate surface through the use of the copolymer, are provided.

DESCRIPTION OF EMBODIMENTS

The present invention is described in more detail below.

A copolymer serving as a subject matter of the present invention is a copolymer that includes a structure represented by the following formula (1), and that is formed of a phosphorylcholine constitutional unit and a photoreactive constitutional unit.

In addition, a copolymer serving as a subject matter of the present invention is a copolymer that includes a structure represented by the following formula (2), and that is formed

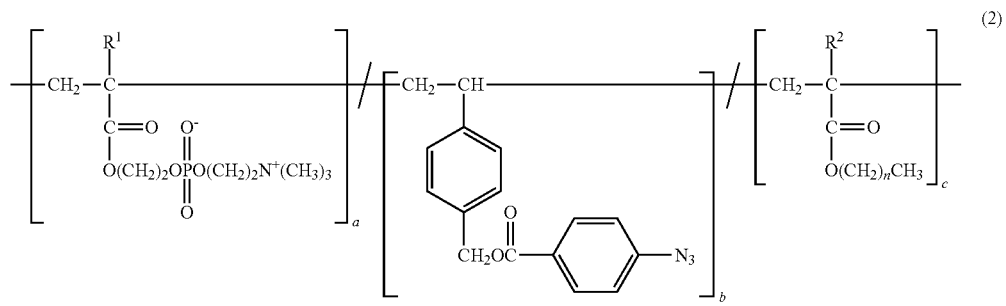

(2)

of a phosphorylcholine constitutional unit, a photoreactive constitutional unit, and a hydrophobic constitutional unit.

containing monomer (see: formula (3)) in its copolymer structure. In the structure of the copolymer, a phosphoryl

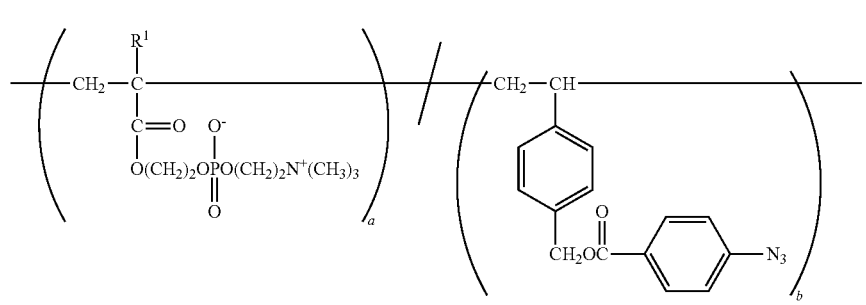

(1)

In the formula (1), $R^1$ represents a hydrogen atom or a methyl group, and a and b represent molar ratios, and satisfy relationships of a/(a+b)=0.75 to 0.99 and b/(a+b)=0.01 to 0.25.

choline group is a polar group having the same structure as that of a phospholipid serving as a main component of a biological membrane. The introduction of a phosphorylcholine group into the copolymer can impart biocompatibility,

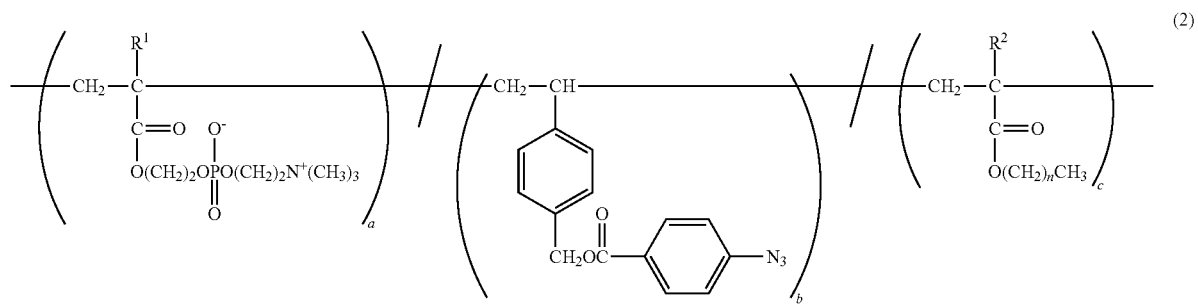

(2)

In the formula (2), $R^1$ and $R^2$ each represent a hydrogen atom or a methyl group, a, b, and c represent molar ratios, and satisfy relationships of a/(a+b+c)=0.30 to 0.98, b/(a+b+c)=0.01 to 0.25, and c/(a+b+c)=0.01 to 0.69, and n represents from 3 to 17.

A surface treatment agent serving as a subject matter of the present invention includes the copolymer of the present invention.

A method of forming a crosslinked body serving as a subject matter of the present invention has a feature of including: coating a substrate surface with the copolymer of the present invention or the surface treatment agent of the present invention; and then irradiating the substrate surface with light to form the crosslinked body on the substrate surface.

A crosslinked body serving as a subject matter of the present invention is obtained by the method of forming a crosslinked body of the present invention, or is obtained by irradiating the copolymer of the present invention or the surface treatment agent of the present invention with light.

A medical device serving as a subject matter of the present invention includes the crosslinked body of the present invention.

The respective constitutional units of the copolymer of the present invention are described below.

[Phosphorylcholine Constitutional Unit]

The copolymer of the present invention includes a constitutional unit based on a phosphorylcholine (PC) group-such as a protein adsorption-suppressing effect, a cell adhesion-suppressing effect, antithrombogenicity, or hydrophilicity, to the copolymer.

Further, when the copolymer is subjected to light treatment or the like on the surface of a substrate, biocompatibility can be imparted to the substrate.

An example of the PC group-containing monomer is 2-(meth)acryloyloxyethyl-2'-(trimethylammonio) ethyl phosphate (also known as: 2-methacryloyloxyethyl-2-trimethylammonioethyl phosphate) (see: formula (8)).

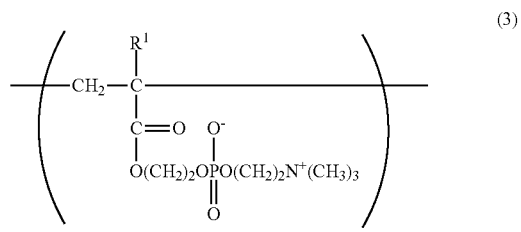

(3)

In the formula (3), $R^1$ represents a hydrogen atom or a methyl group.

[Photoreactive Constitutional Unit]

The copolymer of the present invention includes a constitutional unit containing a photoreactive azidophenyl group (see: formula (4)) in its copolymer structure. The azidophenyl group produces a nitrene rich in reactivity through photoirradiation, and can be bonded to a substrate or a copolymer by abstracting a hydrogen atom therefrom. An azidophenyl group-containing monomer is, for example, 4-(4-azidobenzoyloxymethyl)styrene (see: formula (9), hereinafter sometimes abbreviated as "AzSt").

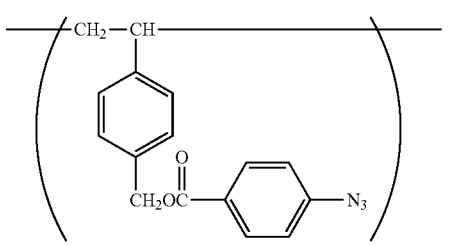
(4)

AzSt may be synthesized by, for example, a substitution reaction between chloromethylstyrene (see: formula (5)) and an alkali metal carboxylate (see: formula (6)), but a synthesis method therefor is not limited thereto.

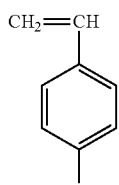
(5)

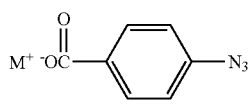
(6)

In the formula (6), M represents an alkali metal.

For example, a product available from AGC Seimi Chemical Co., Ltd. may be used as chloromethylstyrene (hereinafter sometimes abbreviated as "CMS").

The alkali metal carboxylate is prepared from 4-azidobenzoic acid (hereinafter sometimes abbreviated as "ABA") and an alkali metal salt. M in the formula (6) represents an alkali metal, and examples thereof include a lithiumatom, a sodiumatom, and a potassium atom. Of those, a sodium atom or a potassium atom is preferred.

The usage amount of the alkali metal carboxylate is from 0.5 mole to 10 moles, preferably from 1.0 mole to 3.0 moles with respect to 1.0 mole of CMS serving as a raw material. When the usage amount is less than 0.5 mole, CMS serving as a raw material remains, and hence the purity of AzSt reduces in some cases. A case in which the usage amount is more than 10 moles may be disadvantageous in terms of cost owing to an increase in cost of the raw material to be used and a reduction in pot efficiency.

Examples of a solvent to be used in the reaction include: sulfoxides, such as dimethylsulfoxide, and sulfones, such as sulfolane; and amides, such as N,N-dimethylformamide, N,N-dimethylacetamide, and N-methylpyrrolidone. Those solvents may be used alone or as a mixture thereof.

Although an appropriate reaction temperature may be selected as the reaction temperature of the substitution reaction in accordance with reaction conditions, the temperature is preferably from 30° C. to 80° C. in ordinary cases. As the reaction temperature increases, a side reaction becomes more remarkable in some cases. Accordingly, it is important that the reaction be performed at as low a temperature as possible to the extent that the reaction advances at a realistic rate.

After the reaction, AzSt is recovered by extraction and washing operations. The extraction operation is, for example, as follows: the resultant reaction liquid is dissolved in ethyl acetate, and the solution is washed with saline a plurality of times, and as a result, AzSt is extracted in an organic layer. In addition, the use of an alkaline aqueous medium as a washing liquid can efficiently remove unreacted ABA. The alkaline aqueous medium is, for example, a mixed solvent of water and an alkaline solvent (e.g., an aqueous solution of potassium carbonate), but is not particularly limited thereto.

An AzSt solution may be obtained by the above-mentioned operations, and may be purified by chromatography or the like as required. In addition, the solution is desirably stored in a cool dark place in terms of the photoreactivity of AzSt.

[Hydrophobic Constitutional Unit]

The copolymer of the present invention may include a constitutional unit based on a hydrophobic group-containing monomer (see: formula (7)) in its copolymer structure. A hydrophobic group can improve the applicability of the copolymer through its physical adsorption to a hydrophobic substrate surface.

Examples of the hydrophobic group-containing monomer include methacrylic acid esters each having a hydrophobic substituent, such as butyl (meth)acrylate, hexyl (meth)acrylate, 2-ethylhexyl (meth)acrylate, decyl (meth)acrylate, dodecyl (meth)acrylate, tridecyl (meth)acrylate, and stearyl (meth)acrylate (see: formula (10)).

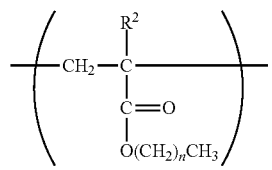
(7)

In the formula (7), $R^2$ represents a hydrogen atom or a methyl group, and n represents from 3 to 17.

When the weight-average molecular weight of the copolymer of the present invention is less than 10,000, it is difficult to purify the polymer, and when the weight-average molecular weight is more than 1,000,000, viscosity at the time of its production becomes so high that it may be difficult to handle the copolymer.

A preferred range of the weight-average molecular weight of the copolymer of the present invention is from 20,000 to 80,000, and a more preferred range thereof is from 23,000 to 75,000.

In the formula (1), a and b represent the constituent ratios of the two constitutional units represented by the formula (3) and the formula (4), that is, the molar ratios of the corresponding monomers.

In the formula (2), a, b, and c represent the constituent ratios of the three constitutional units represented by the formula (3), the formula (4), and the formula (7), that is, the molar ratios of the corresponding monomers.

Here, a, b, and c merely represent the constituent ratios of the constitutional units, and do not mean that the copolymer of the present invention is only a block copolymer formed of blocks represented by the formula (3) and the formula (4), or blocks represented by the formula (3), the formula (4), and the formula (7). The copolymer of the present invention may be a random copolymer of the constitutional units represented by the formula (3) and the formula (4), or the constitutional units (monomers) represented by the formula (3), the formula (4), and the formula (7), may be a block copolymer, or may be a copolymer in which a random moiety and a block moiety are mixed. In addition, an alternating copolymer moiety may be present in the copolymer.

In addition, the ratios a, b, and c representing the constituent ratios of the constitutional units may be arbitrarily adjusted, and are preferably such that the copolymer is soluble in an aqueous medium. Examples of the aqueous medium may include water and a water/alcohol mixed solvent.

The combination of the phosphorylcholine constitutional unit, photoreactive constitutional unit, and hydrophobic constitutional unit of the copolymer of the present invention is as described below, but is not particularly limited (the left portion represents the phosphorylcholine constitutional unit, the central portion represents the photoreactive constitutional unit, and the right portion represents the hydrophobic constitutional unit).

MPC-AzSt

MPC-AzSt-butyl methacrylate

MPC-AzSt-hexyl methacrylate

MPC-AzSt-2-ethylhexyl methacrylate

MPC-AzSt-decyl methacrylate

MPC-AzSt-dodecyl methacrylate

MPC-AzSt-tridecyl methacrylate

MPC-AzSt-stearyl methacrylate

Further, as can be seen from Examples below, a more preferred combination of the phosphorylcholine constitutional unit, photoreactive constitutional unit, and hydrophobic constitutional unit of the copolymer of the present invention is MPC-AzSt-butyl methacrylate (Examples 4 to 6).

Next, an example of a method of producing the copolymer of the present invention is described.

In the copolymer (bipolymer) of the present invention including a structure represented by the formula (1) described above, a copolymer including a structure represented by the formula (1) may be obtained by, for example, polymerizing a monomer composition containing 2-methacryloyloxyethyl-2-trimethylammonioethyl phosphate (MPC) represented by the following formula (8) and AzSt represented by the following formula (9) at the following ratios (polymerization reaction system): the molar ratio of MPC is from 0.75 to 0.99 with respect to the total amount of MPC and AzSt, and the molar ratio of AzSt is from 0.01 to 0.25 with respect thereto.

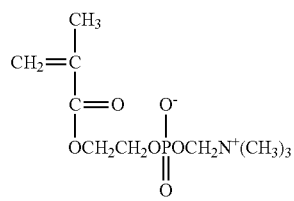

(8)

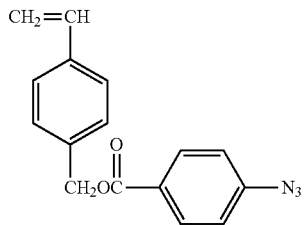

(9)

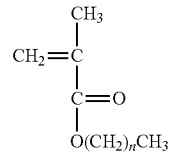

(10)

In the copolymer (terpolymer) of the present invention including a structure represented by the formula (2) described above, a methacrylate ester represented by the formula (10) (n represents from 3 to 17) only needs to be added to the polymerization reaction system.

A copolymer including a structure represented by the formula (2) ($R^1$ and $R^2$ each represent a methyl group, and n represents 3) may be obtained by, for example, polymerizing a monomer composition containing MPC represented by the formula (8), AzSt represented by the formula (9), and butyl methacrylate (BMA) represented by the formula (10: n=3) at the following ratios: the molar ratio of MPC is from 0.30 to 0.98 with respect to the total amount of MPC, AzSt, and BMA, the molar ratio of AzSt is from 0.01 to 0.25 with respect thereto, and the molar ratio of BMA is from 0.01 to 0.69 with respect thereto.

The copolymer may further contain any other copolymerizable monomer as a constituent component.

The polymerization reaction of the monomer composition may be performed by a known method, such as radical polymerization, such as bulk polymerization, suspension polymerization, emulsion polymerization, or solution polymerization, in the presence of, for example, a radical polymerization initiator after the inside of a reaction system has been purged with an inert gas, such as nitrogen, carbon dioxide, argon, or helium, or in the inert gas atmosphere.

The polymerization reaction of the monomer composition is preferably performed by the solution polymerization from the viewpoint of, for example, the purification of the polymer to be obtained. The polymerization reaction provides a copolymer having a structure represented by the formula (1) or the formula (2). As described above, the copolymer of the formula (1) or the formula (2) may be a random copolymer, may be a block copolymer, or may be a copolymer in which a random moiety and a block moiety are mixed. In addition, an alternating copolymer moiety may be present.

In addition, in the bipolymer including a structure represented by the formula (1), a relationship of a/(a+b)=0.75 to 0.99, preferably 0.80 to 0.95, and a relationship of b/(a+b)=0.01 to 0.25, preferably 0.05 to 0.20 are satisfied.

In addition, in the terpolymer including a structure represented by the formula (2), a relationship of a/(a+b+c)=0.30 to 0.98, preferably 0.30 to 0.80, a relationship of b/(a+b+c)=0.01 to 0.25, preferably 0.05 to 0.20, and a relationship of c/(a+b+c)=0.01 to 0.69, preferably 0.05 to 0.65 are satisfied.

As another representation, in the bipolymer including a structure represented by the formula (1), the ratio a of the phosphorylcholine constitutional unit of the copolymer of the present invention and the ratio b of the photoreactive constitutional unit thereof satisfy a ratio "a:b" of 100:1 to 33.

In addition, in the terpolymer including a structure represented by the formula (2), the ratio a of the phosphorylcholine constitutional unit of the copolymer of the present invention, the ratio b of the photoreactive constitutional unit thereof, and the ratio c of the hydrophobic constitutional unit thereof satisfy a ratio "a:b:c" of 100:1 to 83:1 to 230.

Further, as can be seen from Examples below, the ratio a of the phosphorylcholine constitutional unit of the copolymer of the present invention, the ratio b of the photoreactive constitutional unit thereof, and the ratio c of the hydrophobic constitutional unit thereof more preferably satisfy a ratio "a:b:c" of 0.6 to 0.8:0.05 to 0.19:0.01 to 0.30 (Examples 4 to 6).

The purification of those copolymers may be performed by a general purification method, such as a reprecipitation method, a dialysis method, or an ultrafiltration method.

Examples of the radical polymerization initiator include an azo-based radical polymerization initiator, an organic peroxide, and a persulfate.

Examples of the azo-based radical polymerization initiator include 2,2-azobis(2-aminopropyl) dihydrochloride, 2,2-azobis(2-(5-methyl-2-imidazolin-2-yl)propane) dihydrochloride, 4,4-azobis(4-cyanovaleric acid), 2,2-azobisisobutylamide dihydrate, 2,2-azobis(2,4-dimethylvaleronitrile), 2,2-azobisisobutyronitrile (AIBN), dimethyl-2,2'-azobisisobutyrate, 1-((1-cyano-1-methylethyl)azo)formamide, 2,2'-azobis(2-methyl-N-phenylpropionamidine) dihydrochloride, 2,2'-azobis(2-methyl-N-(2-hydroxyethyl)-propionamide), 2,2'-azobis(2-methylpropionamide) dihydrate, 4,4'-azobis(4-cyanopentanoic acid), and 2,2'-azobis(2-(hydroxymethyl) propionitrile).

Examples of the organic peroxide include benzoyl peroxide, diisopropyl peroxydicarbonate, t-butyl peroxy-2-ethylhexanoate, t-butyl peroxypivalate, t-butyl peroxydiisobutyrate, lauroyl peroxide, t-butyl peroxyneodecanoate, succinic acid peroxide (also known as: succinyl peroxide), glutaric peroxide, succinyl peroxyglutarate, t-butyl peroxymalate, t-butyl peroxypivalate, di-2-ethoxyethyl peroxycarbonate, and 3-hydroxy-1,1-dimethylbutyl peroxypivalate.

Examples of the persulfate include ammonium persulfate, potassium persulfate, and sodium persulfate.

Those radical polymerization initiators may be used alone or as a mixture thereof. The usage amount of the polymerization initiator is typically from 0.001 part by mass to 10 parts by mass, preferably from 0.01 part by mass to 5.0 parts by mass with respect to 100 parts by mass of the monomer composition.

The polymerization reaction of the monomer composition may be performed in the presence of a solvent. A solvent that dissolves the monomer composition and does not cause the reaction of the monomer composition before the addition of the polymerization initiator may be used as the solvent. For example, there are given water, an alcohol-based solvent, a ketone-based solvent, an ester-based solvent, an ether-based solvent, and a nitrogen-containing solvent. Examples of the alcohol-based solvent include methanol, ethanol, n-propanol, and isopropanol. Examples of the ketone-based solvent include acetone, methyl ethyl ketone, and diethyl ketone. An example of the ester-based solvent is ethyl acetate. Examples of the ether-based solvent include ethyl cellosolve and tetrahydrofuran. Examples of the nitrogen-containing solvent include acetonitrile, nitromethane, and N-methylpyrrolidone. There are preferably given water, alcohol, and a mixed solvent thereof.

Although a proper temperature only needs to be selected as a temperature at the time of the polymerization reaction as appropriate in accordance with the kinds of the polymerization initiator and the solvent to be used, and a desired molecular weight, the temperature preferably falls within the range of from 40° C. to 100° C.

(Surface Treatment Agent and Method of forming Crosslinked Body of the Present Invention)

The surface treatment agent of the present invention contains 0.01 wt % to 5 wt %, preferably 0.1 wt % to 2.5 wt %, more preferably 0.1 wt % to 1.0 wt % of the copolymer of the present invention.

The surface treatment agent of the present invention contains the copolymer of the present invention, and may contain a proper solvent that can dissolve the copolymer of the present invention, such as water, physiological saline, various buffers (e.g., a phosphate buffer and a carbonate buffer), ethanol, methanol, propanol, or isopropanol, or a mixture thereof.

The method of forming a crosslinked body of the present invention includes: coating a substrate surface with the surface treatment agent of the present invention; and then irradiating the substrate surface with light to form the crosslinked body on the substrate surface.

In the coating with the surface treatment agent of the present invention, a solvent having dissolved therein the copolymer of the present invention (the surface treatment agent of the present invention) only needs to be applied onto a target substrate. It is preferred that the copolymer be caused to exist at 0.01 mg/cm$^2$ (per unit area of the surface of the substrate) or more. In order to form the crosslinked body on the surface of the substrate, the substrate having applied thereto the copolymer only needs to be irradiated with UV light having a wavelength of from 200 nm to 360 nm. The substrate is more preferably irradiated with light having a wavelength of about 254 nm.

The substrate to be used in this case is preferably a substrate that can abstract a hydrogen atom, and examples thereof include various plastic materials, such as polystyrene, polypropylene, polymethyl methacrylate, polyethylene, cyclic polyolefin, polydimethylsiloxane, polyester, and polyurethane. Further, the shape of any such substrate has a shape in accordance with its use purpose. For example, the substrate has a shape such as a plate shape, a tubular shape, a petri dish shape, a shape having many holes, or a shape having formed therein a precise channel.

(Crosslinked Body and Medical Device of the Present Invention)

The crosslinked body formed from the copolymer of the present invention has a three-dimensional network structure in which polymer chains are crosslinked, is excellent in biocompatibility, hydrophilicity, hydrous property, structural flexibility, substance absorbability, and the like, and is excellent particularly in biocompatibility. Therefore, the formation of the crosslinked body of the present invention on the substrate surface can impart biocompatibility to the substrate. In general, the biocompatibilityofaphosphorylcholinegroupisbloodcompatibility, which has a feature in that a protein or a cell does not adsorb or adhere to the substrate surface. In addition, through the utilization of those properties, the crosslinked body can be suitably used for medical devices, such as: a drug sustained-release carrier; a cell scaffold; a surface-modifying material; and a wound healing accelerator, such as a hemostatic.

Specific examples of the medical device of the present invention may include: a contact lens; an artificial organ; a substrate functioning as a scaffold for a transplanted cell; a wound dressing agent; a wound healing accelerator; a hemostatic; a drug sustained-release material; a surface-modifying material; a hemostatic; a substrate for a diagnostic agent to be used in immunochromatography, ELISA, or the like; a substrate for cell culture, such as a petri dish, a microplate, a flask, or a bag; a microchannel; and a cell.

The present invention is also directed to a surface treatment method, including using a copolymer having a weight-average molecular weight of from 10,000 to 1,000,000, the copolymer including a structure represented by the formula (1), wherein molar ratios a and b of respective constitutional units in the formula (1) satisfy the following:

a/(a+b)–0.75 to 0.99; and
b/(a+b)=0.01 to 0.25;

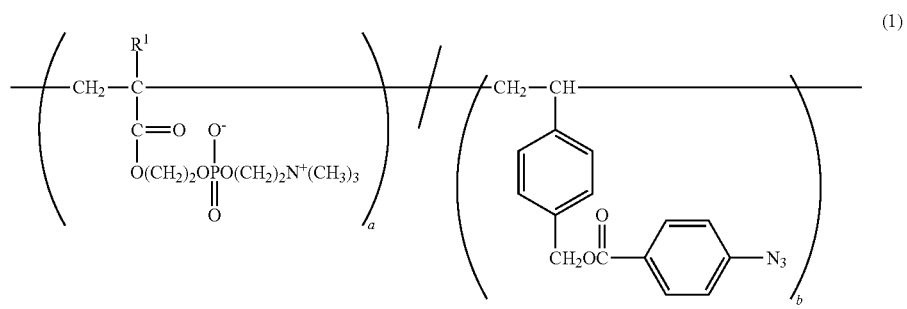

(1)

in the formula (1), $R^1$ represents a hydrogen atom or a methyl group.

The present invention is also directed to a surface treatment method, including using a copolymer having a weight-average molecular weight of from 10,000 to 1,000,000, the copolymer including a structure represented by the formula (2), wherein molar ratios a, b, and c of respective constitutional units in the formula (2) satisfy the following:

a/(a+b+c)=0.30 to 0.98;
b/(a+b+c)=0.01 to 0.25; and
c/(a+b+c)=0.01 to 0.69;

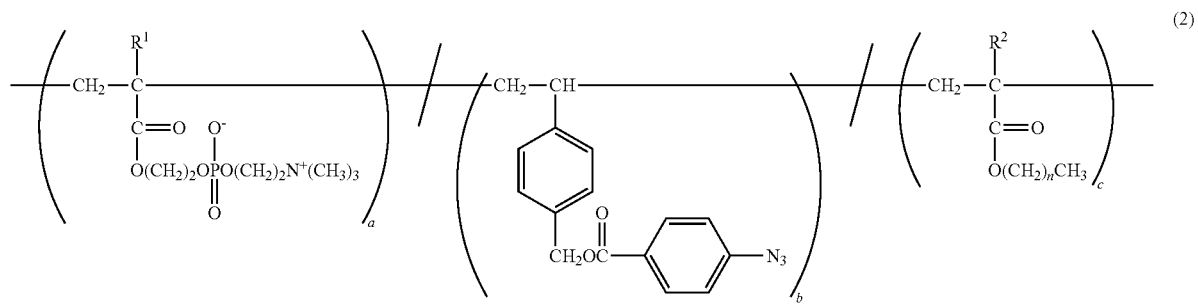

(2)

in the formula (2), $R^1$ and $R^2$ each represent a hydrogen atom or a methyl group, and n represents from 3 to 17.

The present invention is also directed to a copolymer for surface treatment having a weight-average molecular weight of from 10,000 to 1,000,000, the copolymer including a structure represented by the formula (1), wherein molar ratios a and b of respective constitutional units in the formula (1) satisfy the following:

a/(a+b)=0.75 to 0.99; and
b/(a+b)=0.01 to 0.25;

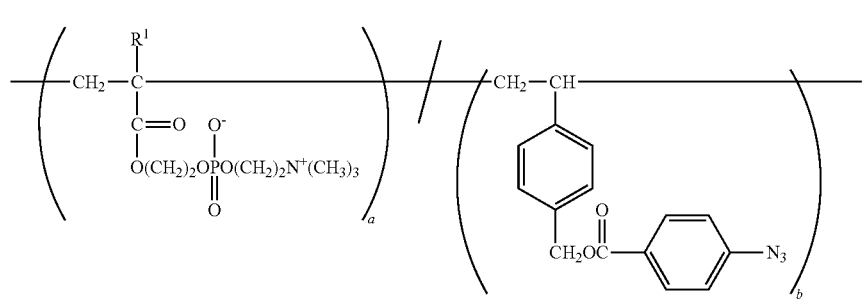

in the formula (1), $R^1$ represents a hydrogen atom or a methyl group.

The present invention is also directed to a copolymer for surface treatment having a weight-average molecular weight of from 10,000 to 1,000,000, the copolymer including a structure represented by the formula (2), wherein molar ratios a, b, and c of respective constitutional units in the formula (2) satisfy the following:

a/(a+b+c)=0.30 to 0.98;
b/(a+b+c)=0.01 to 0.25; and
c/(a+b+c)=0.01 to 0.69;

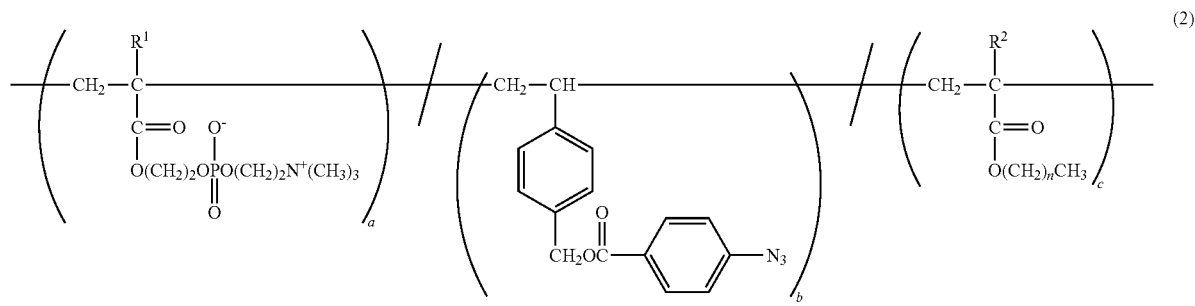

in the formula (2), $R^1$ and $R^2$ each represent a hydrogen atom or a methyl group, and n represents from 3 to 17.

The present invention is also directed to a use of a copolymer having a weight-average molecular weight of from 10,000 to 1,000,000, the copolymer including a structure represented by the formula (1), wherein molar ratios a and b of respective constitutional units in the formula (1) satisfy the following, in production of a surface treatment agent:

a/(a+b)=0.75 to 0.99; and
b/(a+b)=0.01 to 0.25;

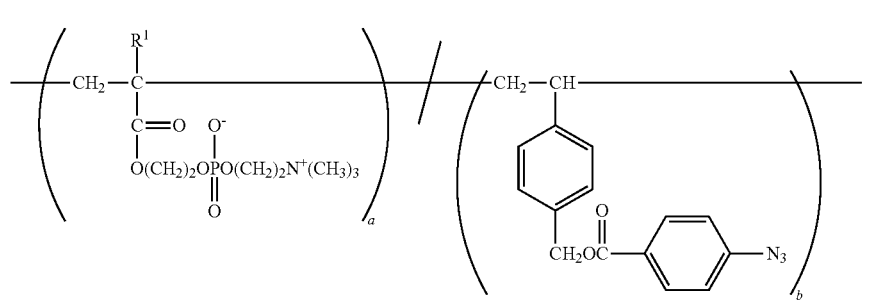

in the formula (1), $R^1$ represents a hydrogen atom or a methyl group.

The present invention is also directed to a use of a copolymer having a weight-average molecular weight of from 10,000 to 1,000,000, the copolymer including a structure represented by the formula (2), wherein molar ratios a, b, and c of respective constitutional units in the formula (2) satisfy the following, in production of a surface treatment agent:

a/(a+b+c)=0.30 to 0.98;
b/(a+b+c)=0.01 to 0.25; and
c/(a+b+c)=0.01 to 0.69;

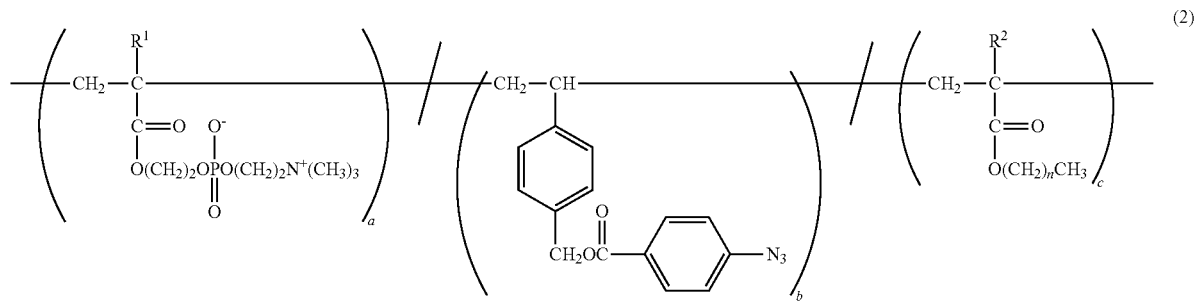

in the formula (2), $R^1$ and $R^2$ each represent a hydrogen atom or a methyl group, and n represents from 3 to 17.

EXAMPLES

Now, the present invention is described in more detail byway of Examples. Various measurements in Examples were performed in accordance with the following methods.

<Measurement of Weight-Average Molecular Weight>

5 mg of the resultant copolymer is dissolved in 1 g of a 0.1 mol/L aqueous solution of sodium sulfate, and its weight-average molecular weight is measured by gel permeation chromatography (GPC). Measurement conditions are as described below.

Apparatus: RI-8020, DP-8020, SD-8022, and AS-8020 (manufactured by Tosoh Corporation), and 865-CO (manufactured by JASCO Corporation), column: Shodex OHpak (manufactured by Showa Denko K.K.), mobile phase: a 0.1 mol/L aqueous solution of sodium sulfate, standard substance: pullulan, detection: a differential refractometer, calculation of weight-average molecular weight (Mw): a molecular weight calculation program (GPC program for SC-8020), flow rate: 1.0 ml/min, column temperature: 40° C., sample solution injection amount: 100 μL, measurement time: 30 minutes.

<$^1$H-NMR Measurement>

20 mg of the resultant copolymer was dissolved in 0.98 g of heavy water, and its $^1$H-NMR was measured.

Apparatus: JNM-ECS400 (manufactured by JEOL Ltd.)
Solvent: Heavy water
Measurement temperature: 60° C.
Relaxation time: 15 s
Number of scans: 32 scans <Infrared Absorbance (IR) Measurement>

20 mg of the resultant copolymer was dissolved in 0.98 g of methanol. Several droplets of the solution were dropped on a NaCl plate, and were dried, followed by the measurement of the infrared absorbance of the copolymer.

Apparatus: FT/IR-6600 (manufactured by JASCO Corporation)
Number of scans: 16 scans 1. Synthesis of Copolymer Synthesis of 4-(4-Azidobenzoyloxymethyl)styrene (AzSt)

6.42 g (0.039 mol) of azidobenzoic acid and 64 g of dimethylsulfoxide were weighed in a 200-milliliter recovery flask, and a temperature in the flask was increased to 50° C. to dissolve the materials. 2.72 g (0.020 mol) of potassium carbonate was added to the solution, and the mixture was stirred for 30 minutes. After a lapse of time, 5.46 g (0.036 mol) of chloromethylstyrene was added to the mixture, and a reaction was performed for 8 hours. After a lapse of 8 hours, 193.15 g of ethyl acetate was added to the resultant, and the organic layer was washed with 63.95 g of saturated saline five times, and was separated and extracted. The organic layer was dehydrated with sodium sulfate, and was then concentrated to provide 17.8 g of AzSt (yield: 89% (50 wt % ethyl acetate solution)).

Thus, AzSt was able to be synthesized by a reaction between chloromethylstyrene and azidobenzoic acid. Further, in the synthesis, there is no need to use a halogen solvent or an acid chloride, and hence a photoreactive azide group-containing copolymer can be synthesized by a method by which the copolymer can be stably supplied even in an industrial scale.

[Synthesis of Copolymer of Example 1]

38.10 g (0.129 mol) of 2-methacryloyloxyethyl-2-trimethylammonioethyl phosphate (MPC) and 3.80 g (6.80 mmol) of a 50 wt % solution of 4-(4-azidobenzoyloxymethyl)styrene (AzSt) in ethyl acetate (EtOAc) were dissolved in 152.24 g of 1-propanol (nPA). The solution was loaded into a 300-milliliter four-necked flask with a temperature gauge and a condenser, and nitrogen was blown into the flask for 30 minutes. After that, 5.90 g (3.59 mmol) of a 10 wt % solution of azobisisobutyronitrile (AIBN) in nPA was added to the solution at 60° C., and a polymerization reaction was performed for 4 hours. After that, the temperature was increased to 70° C., and a reaction was further performed for 2 hours to provide a copolymer. After the completion of the reaction, the copolymer was purified by precipitation in diethyl ether. The $^1$H-NMR, IR, and weight-average molecular weight of the resultant copolymer were measured. The measurement result of the weight-average molecular weight is shown in Table 1.

<Confirmation of Synthesis of Copolymer of Example 1>
($^1$H-NMR)

0.70-1.60 ppm (—C$\underline{H_3}$), 1.60-2.70 ppm (—C$\underline{H_2}$—C, —C$\underline{H_2}$—CH(Ar)—), 3.30-3.85 ppm (—N$^+$((C$\underline{H_3}$)$_3$), 3.85-4.15 ppm (—C$\underline{H_2}$—N$^+$(CH$_3$)$_3$), 4.15-5.00 ppm (—P—O—C$\underline{H_2}$—, —C(O)—O—C$\underline{H_2}$—CH$_2$—, —O—C$\underline{H_2}$—CH$_2$O—P—), 5.20-6.10 ppm (—Ar—C$\underline{H_2}$—), 7.00-8.00 ppm (—CH—Ar$\underline{H}$—CH$_2$—, —O—C(O)—Ar$\underline{H}$), 8.00-8.80 ppm (—O—C(O)—Ar$\underline{H}$)

(IR)

2,957 cm$^{-1}$ (C—H), 2,124 cm$^{-1}$ (—N$_3$), 1,722 cm$^{-1}$ (C=O), 1,235 cm$^{-1}$ $^{(P=O)}$, 1,085 cm$^{-1}$ (—OOCH$_2$—) 968 cm$^{-1}$ (—N$^+$(CH$_3$)$_3$) [Synthesis of Copolymer of Example 2]

A copolymer was synthesized by the same procedure as that of Example 1 except that the feed composition of MPC and AzSt was changed as shown in Table 1. The measurement result of the weight-average molecular weight of the copolymer is shown in Table 1.

[Synthesis of Copolymer of Example 3]

18.17 g (0.0615 mol) of MPC, 5.74 g (0.0103 mol) of a 50 wt % solution of AzSt in ethyl acetate, and 18.96 g (0.133 mol) of butyl methacrylate (BMA) were dissolved in 151.27 g of nPA. The solution was loaded into a 300-milliliter four-necked flask with a temperature gauge and a condenser, and nitrogen was blown into the flask for 30 minutes. After that, 5.90 g (3.59 mmol) of a 10 wt % solution of AIBN in nPA was added to the solution at 60° C., and a polymerization reaction was performed for 4 hours. After that, the temperature was increased to 70° C., and a reaction was further performed for 2 hours to provide a copolymer. After the completion of the reaction, the copolymer was purified by precipitation in diethyl ether. The $^1$H-NMR, IR, and weight-average molecular weight of the resultant copolymer were measured. The measurement result of the weight-average molecular weight is shown in Table 1.

<Confirmation of Synthesis of Copolymer of Example 3>
($^1$H-NMR)

0.70-1.60 ppm (—C$\underline{H_3}$), 1.60-2.70 ppm (—C$\underline{H_2}$⇒C, —C(O)—O—C$\underline{H_2}$—C$\underline{H_2}$—C$\underline{H_2}$—CH$_3$, —C$\underline{H_2}$—CH(Ar)—), 3.30-3.85 ppm (—N$^+$(C$\underline{H_3}$)$_3$), 3.85-4.15 ppm (—C$\underline{H_2}$—N$^+$(CH$_3$)$_3$), 4.15-5.00 ppm (—P—O—C$\underline{H_2}$—, —C(O)—O—C$\underline{H_2}$—CH$_2$—, —O—C$\underline{H_2}$—CH$_2$—O—P—), 5.20-6.10 ppm (—Ar—C$\underline{H_2}$), 7.00-8.00 ppm (—CH—Ar$\underline{H}$—CH$_2$—, —O—C(O)—Ar$\underline{H}$), 8.00-8.80 ppm (—O—C(O)—Ar$\underline{H}$)

(IR)

2,957 cm$^{-1}$ (C—H), 2,123 cm$^{-1}$ (—N$_3$), 1,722 cm$^{-1}$ (C=O), 1,235 cm$^{-1}$ (P=O), 1,086 cm$^{-1}$ (—OPOCH$_2$—), 967 cm$^{-1}$ (—N$^+$(CH$_3$)$_3$)

[Synthesis of Copolymers of Examples 4 to 7]

Copolymers were each synthesized by the same procedure as that of Example 3 except that the feed composition of MPC, AzSt, and BMA was set as shown in Table 1. The measurement results of the weight-average molecular weights of the copolymers are shown in Table 1.

[Synthesis of Copolymer of Example 8]

A copolymer was synthesized by the same procedure as that of Example 3 except that BMA in Example 3 was changed to stearyl methacrylate (SMA). The measurement result of the weight-average molecular weight of the copolymer is shown in Table 1.

[Synthesis of Copolymer of Comparative Example 1]

40.00 g (0.136 mol) of MPC was dissolved in 155.11 g of EtOH. The solution was loaded into a 300-milliliter four-necked flask with a temperature gauge and a condenser, and nitrogen was blown into the flask for 30 minutes. After that, 4.90 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The weight-average molecular weight of the resultant polymer was measured. The measurement result of the weight-average molecular weight is shown in Table 2.

[Synthesis of Copolymer of Comparative Example 2]

35.94 g (0.122 mol) of MPC and 4.06 g (0.0286 mol) of BMA were dissolved in 155.11 g of EtOH. The solution was loaded into a 300-milliliter four-necked flask with a temperature gauge and a condenser, and nitrogen was blown into the flask for 30 minutes. After that, 4.90 g (2.98 mmol) of a 10 wt % solution of AIBN in EtOH was added to the solution at 65° C., and a polymerization reaction was performed for 6 hours. Thus, a copolymer formed of the monomer feed composition was obtained. After the completion of the reaction, the copolymer was purified by precipitation in diethyl ether. The weight-average molecular weight of the resultant copolymer was measured. The measurement result of the weight-average molecular weight is shown in Table 2.

[Synthesis of Copolymer of Comparative Example 3]

18.20 g (0.0616 mol) of MPC and 1.20 g (7.25 mmol) of aminoethyl methacrylate (AEMA) free of any benzophenone group were dissolved in 80.00 g of ion-exchanged water (PW). The solution was loaded into a 300-milliliter four-necked flask with a temperature gauge and a condenser, and nitrogen was blown into the flask for 30 minutes. After that, 0.15 g (0.550 mmol) of 2,2'-azobis(2-methylpropionamidine) dihydrochloride (V-50) was added to the solution at 60° C., and a polymerization reaction was performed for 8 hours. Thus, a copolymer formed of the monomer feed composition was obtained. After the completion of the reaction, the copolymer was purified by dialysis. The weight-average molecular weight of the resultant copolymer was measured. The measurement result of the weight-average molecular weight is shown in Table 2.

2. Evaluation of Copolymer

The copolymers of the present invention and the (co)polymers except those of the present invention described above were evaluated by the following methods. The results of the copolymers of Examples are shown in Table 1, and the results of the (co)polymers of Comparative Examples are shown in Table 2.

[Evaluation of Protein Adsorption Ratio]

Each copolymer was dissolved in ethanol so that its concentration became 0.5 wt %, and a copolymer coating was formed on each well bottom surface of a 96-well plate made of polystyrene (manufactured by Watson Biolab) so that a predetermined copolymer amount c (unit: mg/cm$^2$) was obtained. After that, the plate was irradiated with light having a wavelength of 254 nm for 7 minutes by using DNA-FIX (manufactured by ATTO Corporation). After the photoirradiation, ethanol was added in an amount of 200 μL/well, and the plate was left at rest at room temperature for 3 hours. After that, ethanol was removed, and fresh ethanol was added in an amount of 200 μL/well and removed; the washing step was performed three times. After the washing with ethanol, horseradish peroxidase-labeled IgG (manufactured by Bio-Rad Laboratories, Inc.) diluted 24,000-fold with a phosphate buffer was added in an amount of 100 μL/well, and the plate was left at rest at room temperature for 1 hour. After a lapse of 1 hour, the HRP-labeled IgG solution in each well was removed, and a phosphate buffer containing 0.05% Tween 20 was added in an amount of 200 μL/well and removed; the washing step was repeated four times. After the washing, a chromogenic liquid for a peroxidase (manufactured by KPL) was added in an amount of 100 μL/well, and a reaction was performed at room temperature for 10 minutes. After a lapse of 10 minutes, 2 N sulfuric acid was added in an amount of 50 μL/well to terminate the reaction, and an absorbance at 450 nm was measured with a microplate reader. Thus, the peroxidase (protein) adsorbing to the inside of each well was detected.

As a control, the same operations as those described above were performed by using water instead of the solution of the copolymer in ethanol, and the obtained result was defined as Comparative Example 4.

A protein adsorption ratio was evaluated at the following three levels: the copolymer amount c on each well bottom surface=0.06 mg/cm$^2$, 0.24 mg/cm$^2$, or 0.36 mg/cm$^2$. The absorbance of the well free of any copolymer coating (Comparative Example 4) was defined as a protein adsorption ratio of 100%, and the protein adsorption ratios of Examples and Comparative Examples were calculated.

[Evaluation of Cell Adhesion Ratio]

Each copolymer was dissolved in ethanol so that its concentration became 0.5 wt %, and a copolymer coating was formed on each well bottom surface of a 24-well plate made of polystyrene (manufactured by Nunc) so that a predetermined copolymer amount c (unit: mg/cm$^2$) was obtained. After that, the plate was irradiated with light having a wavelength of 254 nm for 7 minutes by using DNA-FIX (manufactured by ATTO Corporation). After the photoirradiation, ethanol was added in an amount of 400 μL/well, and the plate was left at rest at room temperature for 15 hours. After that, ethanol was removed, and fresh ethanol was added in an amount of 400 μL/well and removed; the washing step was performed three times. After that, Dulbecco's Phosphate Buffered Saline (hereinafter referred to as "D-PBS") that had already been sterilized was added in an amount of 400 μL/well in a clean bench and removed; the washing step was performed three times.

Mouse embryonic fibroblasts (NIH3T3 cells) cultured in Dulbecco's Modified Eagle Medium containing 10% calf serum and penicillin-streptomycin (hereinafter referred to as "medium for 3T3") were inoculated in an amount of 10,000 cells/well (400 μL/well), and were cultured in a $CO_2$ incubator at 37° C. for 3 days. After a lapse of 3 days, the supernatant was removed, and the D-PBS was added in an amount of 400 μL/well and removed; the washing step was performed twice. After the washing, a product obtained by mixing WST-8 (manufactured by Kishida Chemical Co., Ltd.) and the medium for 3T3 at a ratio of 1:9 was added in an amount of 400 μL/well, and was cultured in a $CO_2$ incubator at 37° C. for 3 hours. After a lapse of 3 hours, 150 μL of the supernatant was recovered in a flat-bottom 96-well plate made of polystyrene (manufactured by Nunc), and its absorbance at 570 nm was measured with a microplate reader. Thus, the cells adhering to the bottom surfaces of the wells were detected.

As a control, the same operations as those described above were performed by using water instead of the solution of the copolymer in ethanol (Comparative Example 4).

A cell adhesion ratio was evaluated at the following four levels: the copolymer amount c on each well bottom surface=0.01 mg/cm$^2$, 0.10 mg/cm$^2$, 0.25 mg/cm$^2$, or 0.50 mg/cm$^2$. The absorbance of the well free of any copolymer coating (Comparative Example 4) was defined as a cell adhesion ratio of 100%, and the cell adhesion ratios of Examples and Comparative Examples were calculated.

TABLE 1

| | | | | Example 1 | Example 2 | Example 3 | Example 4 | Example 5 | Example 6 | Example 7 | Example 8 |
|---|---|---|---|---|---|---|---|---|---|---|---|
| Component for synthesizing copolymer | Monomer (g) | A | MPC | 38.10 | 32.35 | 18.17 | 28.60 | 32.50 | 34.80 | 35.52 | 31.70 |
| | | B | AzSt | 1.90 | 7.65 | 2.87 | 4.51 | 7.30 | 2.06 | 0.42 | 3.75 |
| | | C | BMA | — | — | 18.96 | 6.89 | 0.20 | 3.14 | 4.06 | — |
| | | | SMA | — | — | — | — | — | — | — | 4.55 |
| | Others | | AEMA | — | — | — | — | — | — | — | — |
| | Solvent (g) | | nPA | 157.55 | 151.76 | 156.58 | 154.90 | 152.11 | 157.36 | 158.99 | 155.66 |
| | | | EtOH | — | — | — | — | — | — | — | — |
| | | | PW | — | — | — | — | — | — | — | — |
| | | | EtOAc | 1.90 | 7.65 | 2.87 | 4.51 | 7.30 | 2.06 | 0.42 | 3.75 |
| | Initiator (g) | | AIBN | 0.59 | 0.59 | 0.59 | 0.59 | 0.59 | 0.59 | 0.59 | 0.59 |
| | | | V-50 | — | — | — | — | — | — | — | — |
| | Molar ratio of each constitutional unit | | a | 0.95 | 0.80 | 0.30 | 0.60 | 0.80 | 0.80 | 0.80 | 0.80 |
| | | | b | 0.05 | 0.20 | 0.05 | 0.10 | 0.19 | 0.05 | 0.01 | 0.10 |
| | | | c | 0 | 0 | 0.65 | 0.30 | 0.01 | 0.15 | 0.19 | 0.10 |
| | | | Others | 0 | 0 | 0 | 0 | 0 | 0 | 0 | 0 |
| Evaluation result of copolymer | Weight-average molecular weight (Mw) | | | 72,000 | 63,000 | 12,000 | 25,000 | 50,000 | 49,000 | 33,000 | 28,000 |
| | Protein adsorption ratio [%] Numerical value in ( ) represents absorbance (450 nm) | [c = 0.06] * | | 16.7 (0.289) | 15.2 (0.262) | 14.1 (0.244) | 5.7 (0.098) | 5.4 (0.093) | 3.8 (0.065) | 9.4 (0.162) | 9.7 (0.168) |
| | | [c = 0.24] * | | 14.6 (0.253) | 11.7 (0.202) | 11.5 (0.198) | 3.8 (0.066) | 4.2 (0.073) | 3.6 (0.062) | 8.6 (0.148) | 9.6 (0.165) |
| | | [c = 0.36] * | | 14.0 (0.241) | 10.3 (0.178) | 9.7 (0.167) | 3.5 (0.060) | 3.1 (0.053) | 2.8 (0.049) | 8.2 (0.142) | 9.1 (0.158) |

TABLE 1-continued

|  |  | Example 1 | Example 2 | Example 3 | Example 4 | Example 5 | Example 6 | Example 7 | Example 8 |
|---|---|---|---|---|---|---|---|---|---|
| Cell adhesion ratio [%] Numerical value in ( ) represents absorbance (570 nm) | [c = 0.01] * | 2.1 (0.070) | 1.7 (0.056) | 0.8 (0.026) | 1.1 (0.036) | 0.6 (0.019) | 0.9 (0.029) | 0.8 (0.028) | 1.2 (0.038) |
|  | [c = 0.10] * | 2.0 (0.065) | 0.9 (0.029) | 1.0 (0.033) | 0.5 (0.018) | 1.0 (0.032) | 1.8 (0.060) | 1.0 (0.032) | 1.6 (0.054) |
|  | [c = 0.25] * | 1.3 (0.042) | 1.2 (0.038) | 1.5 (0.048) | 0.8 (0.025) | 0.8 (0.028) | 1.7 (0.056) | 1.0 (0.034) | 1.1 (0.036) |
|  | [c = 0.50] * | 0.8 (0.028) | 1.1 (0.035) | 1.7 (0.056) | 0.8 (0.028) | 0.8 (0.025) | 1.1 (0.035) | 0.9 (0.030) | 1.0 (0.034) |

TABLE 2

|  |  |  |  | Comparative Example 1 | Comparative Example 2 | Comparative Example 3 | Comparative Example 4 |
|---|---|---|---|---|---|---|---|
| Component for synthesizing (co)polymer | Monomer (g) | A | MPC | 40.00 | 35.94 | 18.20 | No copolymer is used and water is used as aqueous solution |
|  |  | B | AzSt | — | — | — |  |
|  |  | C | BMA | — | 4.06 | — |  |
|  |  |  | SMA | — | — | — |  |
|  |  | Others | AEMA | — | — | 1.20 |  |
|  | Solvent (g) |  | nPA | — | — | — |  |
|  |  |  | EtOH | 159.52 | 159.52 | — |  |
|  |  |  | PW | — | — | 80.00 |  |
|  |  |  | EtOAc | — | — | — |  |
|  | Initiator (g) |  | AIBN | 0.49 | 0.49 | — |  |
|  |  |  | V-50 | — | — | 0.15 |  |
|  | Molar ratio of each constitutional unit |  | a | 1.00 | 0.81 | 0.89 |  |
|  |  |  | b | 0 | 0 | 0 |  |
|  |  |  | c | 0 | 0.19 | 0 |  |
|  |  |  | Others | 0 | 0 | 0.11 |  |
| Evaluation result of (co)polymer | Weight-average molecular weight (Mw) |  |  | 188,000 | 138,000 | 800,000 |  |
|  | Protein adsorption ratio [%] Numerical value in ( ) represents absorbance (450 nm) | [c = 0.06] * |  | 93.8 (1.620) | 90.0 (1.554) | 96.0 (1.658) | 100 (1.727) |
|  |  | [c = 0.24] * |  | 95.5 (1.650) | 88.7 (1.532) | 94.5 (1.632) | [c = 0] * |
|  |  | [c = 0.36] * |  | 92.1 (1.590) | 84.5 (1.460) | 93.3 (1.612) |  |
|  | Cell adhesion ratio [%] Numerical value in ( ) represents absorbance (570 nm) | [c = 0.01] * |  | 96.6 (3.185) | 97.0 (3.198) | 98.7 (3.254) | 100 (3.296) |
|  |  | [c = 0.10] * |  | 96.6 (3.183) | 96.6 (3.185) | 96.6 (3.183) | [c = 0] * |
|  |  | [c = 0.25] * |  | 97.7 (3.220) | 94.7 (3.120) | 96.6 (3.185) |  |
|  |  | [c = 0.50] * |  | 98.9 (3.259) | 93.6 (3.085) | 95.8 (3.156) |  |

* c in each table represents a copolymer amount (mg/cm$^2$).

As is apparent from the results of the protein adsorption ratios in Tables 1 and 2, it was confirmed that when the crosslinked body obtained from each of the copolymers of Examples 1 to 8 was formed on the substrate surface, and the resultant was irradiated with light, the substrate surface suppressing the adsorption of the protein (horseradish peroxidase-labeled IgG) was able to be formed.

Meanwhile, in each of Comparative Example 1 (polymer that included a phosphorylcholine constitutional unit, but was free of any photoreactive constitutional unit and any hydrophobic constitutional unit), Comparative Example 2 (copolymer that included a phosphorylcholine constitutional unit and a hydrophobic constitutional unit, but was free of any photoreactive constitutional unit), and Comparative Example 3 (copolymer that included a phosphorylcholine constitutional unit and a constitutional unit having an amino group, but was free of any photoreactive constitutional unit and any hydrophobic constitutional unit), the following result was obtained: no copolymer crosslinked body was formed on the substrate surface by the photoirradiation, and hence the protein adhered to the substrate surface.

It was confirmed from the foregoing results that the surface treatment agent of the present invention was able to impart biocompatibility (performance preventing the adsorption of a protein) to a substrate surface through its application to the substrate surface and the irradiation of the substrate surface with light.

Further, as is apparent from the results of the cell adhesion ratios in Tables 1 and 2, it was confirmed that when the crosslinked body obtained from each of the copolymers of Examples 1 to 8 was formed on the substrate surface, and the resultant was irradiated with light, the substrate surface suppressing the adhesion of the mouse embryonic fibroblasts was able to be formed.

Meanwhile, in each of Comparative Example 1 (polymer that included a phosphorylcholine constitutional unit, but was free of any photoreactive constitutional unit and any hydrophobic constitutional unit), Comparative Example 2 (copolymer that included a phosphorylcholine constitutional unit and a hydrophobic constitutional unit, but was free of any photoreactive constitutional unit), and Comparative Example 3 (copolymer that included a phosphorylcholine constitutional unit and a constitutional unit having an amino group, but was free of any photoreactive constitutional unit and any hydrophobic constitutional unit), the following result was obtained: no copolymer crosslinked body was formed on the substrate surface by the photoirradiation, and hence the mouse embryonic fibroblasts adhered to the substrate surface.

It was confirmed from the foregoing results that the surface treatment agent of the present invention was able to impart biocompatibility (performance preventing the adsorption of a cell) to a substrate surface through its application to the substrate surface and the irradiation of the substrate surface with light.

It was confirmed from the foregoing results that a protein, a cell, or the like did not adhere to the crosslinked body of the present invention. Accordingly, the surface treatment agent and the medical device including the crosslinked body of the present invention each have high biocompatibility.

INDUSTRIAL APPLICABILITY

The copolymer having biocompatibility sufficient for use in medical material applications, and the method of forming a crosslinked body, the method including imparting biocompatibility to a substrate surface through the use of the copolymer can be provided.

The invention claimed is:

1. A copolymer having a weight-average molecular weight of from 10,000 to 1,000,000, the copolymer comprising a structure represented by the formula (1), wherein molar ratios a and b of respective constitutional units in the formula (1) satisfy the following:

a/(a+b)=0.75 to 0.99; and
b/(a+b)=0.01 to 0.25;

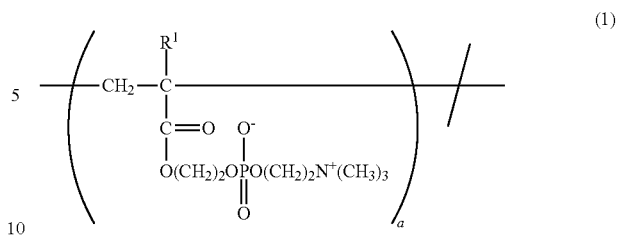

in the formula (1), $R^1$ represents a hydrogen atom or a methyl group.

2. A copolymer having a weight-average molecular weight of from 10,000 to 1,000,000, the copolymer comprising a structure represented by the formula (2), wherein molar ratios a, b, and c of respective constitutional units in the formula (2) satisfy the following:

a/(a+b+c)=0.30 to 0.98;
b/(a+b+c)=0.01 to 0.25; and
c/(a+b+c)=0.01 to 0.69;

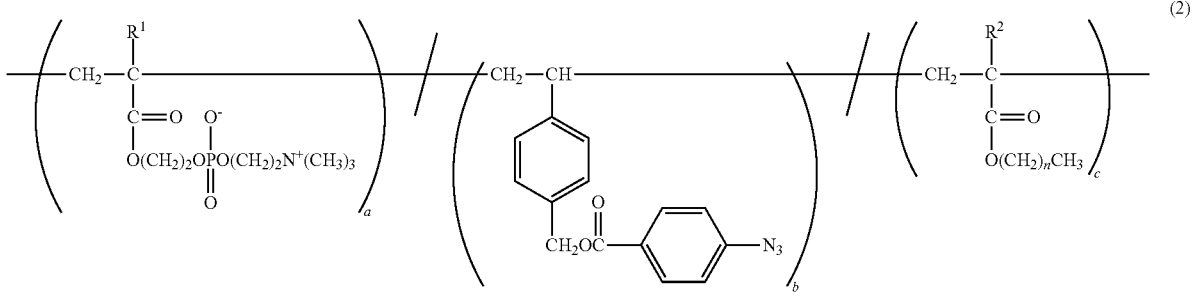

in the formula (2), $R^1$ and $R^2$ each represent a hydrogen atom or a methyl group, and n represents from 3 to 17.

3. A copolymer according to claim 1, wherein the copolymer comprises a constitutional unit based on 2-methacryloyloxyethyl-2-trimethylammonioethyl phosphate and a constitutional unit based on 4-(4-azidobenzoyloxymethyl) styrene.

4. A copolymer according to claim 2, wherein the copolymer comprises a constitutional unit based on 2-methacryloyloxyethyl-2-trimethylammonioethyl phosphate, a constitutional unit based on 4-(4-azidobenzoyloxymethyl)styrene, and a constitutional unit based on butyl methacrylate.

5. A copolymer according to claim 2, wherein the copolymer comprises a constitutional unit based on 2-methacryloyloxyethyl-2-trimethylammonioethyl phosphate, a constitutional unit based on 4-(4-azidobenzoyloxymethyl)styrene, and a constitutional unit based on stearyl methacrylate.

6. A surface treatment agent, comprising the copolymer of claim 1.

7. A surface treatment agent, comprising the copolymer of claim 2.

8. A surface treatment agent according to claim 6, wherein the surface treatment agent comprises a surface treatment agent for suppressing protein adsorption.

9. A surface treatment agent according to claim 7, wherein the surface treatment agent comprises a surface treatment agent for suppressing protein adsorption.

10. A surface treatment agent according to claim 6, wherein the surface treatment agent comprises a surface treatment agent for suppressing cell adhesion.

11. A surface treatment agent according to claim 7, wherein the surface treatment agent comprises a surface treatment agent for suppressing cell adhesion.

12. A method of forming a crosslinked body, comprising:
    coating a substrate surface with the copolymer of claim 1; and
    then irradiating the substrate surface with light to form the crosslinked body on the substrate surface.

13. A method of forming a crosslinked body, comprising:
    coating a substrate surface with the copolymer of claim 2; and
    then irradiating the substrate surface with light to form the crosslinked body on the substrate surface.

14. A method of forming a crosslinked body, comprising:
    coating a substrate surface with the surface treatment agent of claim 6; and
    then irradiating the substrate surface with light to form the crosslinked body on the substrate surface.

15. A method of forming a crosslinked body, comprising:
    coating a substrate surface with the surface treatment agent of claim 7; and
    then irradiating the substrate surface with light to form the crosslinked body on the substrate surface.

16. A crosslinked body, which is obtained by the method of forming a crosslinked body of claim 12.

17. A crosslinked body, which is obtained by irradiating the copolymer of claim 1 with light.

18. A medical device, comprising the crosslinked body of claim 16.

* * * * *